United States Patent
Elowe et al.

(10) Patent No.: US 8,907,136 B2
(45) Date of Patent: Dec. 9, 2014

(54) CATALYSTS AND METHODS FOR ALCOHOL DEHYDRATION

(71) Applicant: Dow Global Technologies LLC, Midland, MI (US)

(72) Inventors: Paul R. Elowe, Midland, MI (US); David G. Barton, Midland, MI (US); Adam Chojecki, Ghent (BE); Joost Depicker, Wachtebeke (BE)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/359,527

(22) PCT Filed: Nov. 20, 2012

(86) PCT No.: PCT/US2012/065969
§ 371 (c)(1),
(2), (4) Date: May 20, 2014

(87) PCT Pub. No.: WO2013/095850
PCT Pub. Date: Jun. 27, 2013

(65) Prior Publication Data
US 2014/0306145 A1  Oct. 16, 2014

Related U.S. Application Data

(60) Provisional application No. 61/577,749, filed on Dec. 20, 2011.

(51) Int. Cl.
*C07C 41/09* (2006.01)
*C07C 43/275* (2006.01)
*C09K 5/10* (2006.01)
*C09K 5/00* (2006.01)

(52) U.S. Cl.
CPC . *C07C 41/09* (2013.01); *C09K 5/10* (2013.01); *C09K 5/00* (2013.01)
USPC .......................................................... 568/635

(58) Field of Classification Search
CPC ....................................................... C07C 41/09
USPC .......................................................... 568/635
See application file for complete search history.

(56) References Cited

U.S. PATENT DOCUMENTS

| | | | |
|---|---|---|---|
| 1,873,537 A * | 8/1932 | Brown et al. | 568/635 |
| 5,288,922 A | 2/1994 | Buske et al. | |
| 5,925,798 A | 7/1999 | Gambell et al. | |

FOREIGN PATENT DOCUMENTS

| | | | | |
|---|---|---|---|---|
| GB | 649999 | * | 4/1949 | |
| JP | 02085224 A | * | 3/1990 | C07C 43/04 |
| WO | 0015730 | | 3/2000 | |

* cited by examiner

*Primary Examiner* — Rosalynd Keys
(74) *Attorney, Agent, or Firm* — Steven W. Mork

(57) ABSTRACT

Provided is a method for preparing a diaryl ether compound through the dehydration of an aromatic alcohol compound in the presence of a dehydration catalyst. The dehydration catalyst comprises an oxide of yttrium.

9 Claims, No Drawings

US 8,907,136 B2

CATALYSTS AND METHODS FOR ALCOHOL DEHYDRATION

CROSS-REFERENCE TO RELATED APPLICATIONS

This application claims priority from provisional application Ser. No. 61/577,749, filed Dec. 20, 2011, which is incorporated herein by reference in its entirety.

BACKGROUND

This invention relates generally to catalysts and methods for the dehydration of aromatic alcohol compounds to ethers. More particularly, the invention uses a catalyst comprising an oxide of yttrium for the dehydration of aromatic alcohol compounds to diaryl ethers.

Diaryl ethers are an important class of industrial materials. Diphenyl oxide (DPO), for instance, has many uses, most notably as the major component of the eutectic mixture of DPO and biphenyl, which is the standard heat transfer fluid for the concentrating solar power (CSP) industry. With the current boom in CSP has come a tightening of the supply of DPO globally and questions surrounding the sustainability of the technology have arisen.

Diaryl ethers are currently manufactured commercially via two major routes: gas-phase dehydration of an aryl alcohol, or reaction of a haloaryl compound with an aryl alcohol. The latter route, for example where chlorobenzene reacts with phenol in the presence of caustic and a copper catalyst, typically leads to less pure product and requires high pressure (5000 psig), uses an expensive alloy reactor and produces stoichiometric quantities of sodium chloride. The former, more desirable approach, accounts for the largest volume of diaryl ethers produced but requires a very active and selective catalytic material.

For instance, DPO can be manufactured by the gas-phase dehydration of phenol over a thorium oxide (thoria) catalyst (e.g., U.S. Pat. No. 5,925,798). A major drawback of thoria however is its radioactive nature, which makes its handling difficult and potentially costly. Furthermore, the supply of thoria globally has been largely unavailable in recent years putting at risk existing DPO manufacturers utilizing this technology. Additionally, other catalysts for the gas-phase dehydration of phenol, such as zeolite catalysts, titanium oxide, zirconium oxide and tungsten oxide, generally suffer from lower activity, significantly higher impurity content and fast catalyst deactivation.

With a chronic shortage of diaryl ethers such as DPO in sight and a pressing need to increase capacity, it has become crucial to develop alternate methods to produce such materials in a cost-effective and sustainable manner.

The problem addressed by this invention, therefore, is the provision of new catalysts and methods for manufacture of diaryl ethers from aryl alcohol compounds.

STATEMENT OF INVENTION

We have now found that a catalyst comprising an oxide of yttrium is effective for the preparation of diaryl ethers from aromatic alcohol compounds. Advantageously, the catalyst exhibits remarkable selectivity for the desired product. Moreover, since various oxides of yttrium are abundant globally, relatively inexpensive and non-radioactive, this invention represents a unique solution for diaryl ether supply issues globally.

In one aspect, there is provided a method for preparing a diaryl ether, the method comprising dehydrating an aromatic alcohol compound over a dehydration catalyst, wherein the dehydration catalyst comprises an oxide of yttrium.

In another aspect, there is provided a method for producing a heat transfer fluid, the method comprising: preparing a diaryl ether by contacting an aromatic alcohol compound with a dehydration catalyst, wherein the dehydration catalyst comprises an oxide of yttrium; isolating the diaryl ether from the dehydration catalyst; and mixing the isolated diaryl ether with biphenyl, wherein the mixture forms a eutectic mixture.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

As noted above, in one aspect the invention provides a method for producing a diaryl ether by dehydrating an aromatic alcohol compound over an yttrium based dehydration catalyst. It has been discovered that such catalysts exhibit high selectivity for the desired diaryl ether compounds with relatively low formation of undesirable byproducts. For instance, as demonstrated by the examples, in the synthesis of diphenyl oxide from phenol, a selectivity for the DPO of 50% or greater may be achieved. In some embodiments, a selectivity of 85% or greater may be achieved. In some embodiments, a selectivity of 90% or greater, alternatively 95% or greater, or alternatively 99% or greater is possible. In some embodiments, a selectivity of 100% for the DPO is possible.

In addition to being highly selective, the catalysts are further advantaged because they are inexpensive. Moreover, the catalysts are non-radioactive, thus eliminating the safety and environmental issues, as well as higher costs, associated with the handling of radioactive materials, such as the thoria catalysts of the prior art.

The dehydration catalyst of the invention comprises an oxide of yttrium. By "oxide of yttrium" is meant a compound that contains at least yttrium and oxygen atoms. An example is yttrium oxide (yttria). The catalyst may optionally contain other atoms, such as halogens, including chloride or fluoride.

A preferred catalyst for use in the invention is an yttrium oxychloride, which is a catalyst that contains metal-oxygen and metal-chlorine bonds. In some embodiments, the catalyst may comprise, in addition to the yttrium and oxygen, chlorine in an amount of less than 54.5 weight percent, alternatively 40 weight percent or less, alternatively 26 weight percent or less, alternatively 10 weight percent or less, or alternatively 2 weight percent or less. In some embodiments, the catalyst comprises the chlorine in an amount of at least 0.001 weight percent, alternatively at least 0.1 weight percent, alternatively at least 1 weight percent, or alternatively at least 2 weight percent. In some embodiments, the catalyst contains between 2 and 26 weight percent chlorine. The chlorine is in the form of chloride ion ($Cl^-$). Non limiting examples of suitable compounds may include YOCl, $Y_4O_5Cl_2$, $Y_3O_4Cl$ or a physical mixture of $YCl_3$—$Y_2O_3$, or yttria containing a chloride (e.g., $NH_4Cl$, HCl) as an additive. Examples further include, again without limitation, yttrium catalysts based on chlorate oxyanions, such as hypochlorite ($ClO^-$); chlorite ($ClO_2^-$); chlorate ($ClO_3^-$), perchlorate ($ClO_4^-$) where Cl is oxidized (+2, +3, +4, +5), as well as amorphous materials. Catalysts suitable for use in the invention may be prepared by those skilled in the art or they may be purchased from commercial vendors.

The catalyst may optionally contain a binder and/or matrix material that is different from the active oxide of yttrium. Non-limiting examples of binders that are useful alone or in combination include various types of hydrated alumina, silicas and/or other inorganic oxide sols, and carbon. Upon heating, the inorganic oxide sol, preferably having a low viscosity, is converted into an inorganic oxide binder component.

Where the catalyst composition contains a matrix material, this is preferably different from the active catalyst and any binder. Non-limiting examples of matrix materials include clays or clay-type compositions.

The catalyst, including any binder or matrix materials, may be unsupported or supported. Non-limiting examples of suitable support materials include titania, alumina, zirconia, silica, carbons and mixtures thereof. Where the catalyst contains a binder, matrix or support material, the amount of oxide of yttrium (the active component of the catalyst) may be between 1 and 99 percent by weight based on the total weight of the catalyst (including the oxide, and any support, binder or matrix materials).

The catalyst may be formed into various shapes and sizes for ease of handling. For instance, the catalyst (plus any binder, matrix, or support) may be in the form of pellets, spheres, or other shapes used in the industry.

Aromatic alcohol compounds suitable for use in the process of this invention include aromatic compounds containing at least one alcohol group and one, two, three or more aromatic moieties. Suitable compounds include phenols and α- and β-hydroxy-substituted fused aromatic ring systems. Apart from the hydroxy substituent, the compounds may be unsubstituted, as in phenol or naphthol. Optionally, however, the compounds may be further substituted with at least one alkyl group containing from 1 to about 10 carbon atoms, preferably, from 1 to 3 carbon atoms, or substituted with at least one alternative substituent which is inert to the dehydration coupling reaction. Suitable inert substituents include cyano, amino, nitro, carboxylic acid (e.g., $C_0$-$C_6$—COOH), ester, $C_6$-$C_{12}$ aryl, $C_2$-$C_6$ alkenyl, alkyloxy and phenoxy moieties. It is also possible for the aromatic alcohol compound to be substituted with both an alkyl substituent and one of the alternative inert substituents. Each of the aforementioned alkyl substituents and/or alternative inert substituents is attached preferably to an aromatic ring carbon atom which is located in a meta or para position relative to the hydroxy moiety. Optionally, the alkyl substituent may contain from 3 to 4 carbon atoms, and in combination with a phenol or fused aromatic ring system may form a saturated ring fused to the aromatic ring. An acceptable feed may contain a mixture of aromatic alcohols, including mixtures of the foregoing.

Non-limiting examples of suitable phenols include unsubstituted phenol, m-cresol, p-cresol, 3,4-xylenol, 3,5-xylenol, and 3,4,5-trimethylphenol. Other suitable phenols include compounds corresponding to the above-mentioned examples except that one or more of the methyl substituents are replaced by an ethyl, propyl or butyl substituent. Non-limiting examples of α- and β-hydroxy-substituted fused aromatic ring systems include α- and β-naphthol and 5-tetralinol. Other non-limiting examples of aromatic alcohols include benzenediols (catechol, resorcinol or hydroquinone), o-cresol, o-phenylphenol, m-phenylphenol or p-phenylphenol. One skilled in the art may find other phenols and α- and β-hydroxy-substituted fused aromatic ring systems which are also suitable for the purposes of this invention. Preferably, the aromatic alcohol is unsubstituted phenol or a substituted phenol wherein the substituent is methyl or ethyl. More preferably, the aromatic alcohol is unsubstituted phenol or cresol. Most preferably, the aromatic alcohol is unsubstituted phenol.

According to the method of the invention for preparing a diaryl ether, a catalyst comprising an oxide of yttrium is contacted with the aromatic alcohol compound. The contacting of the catalyst with the aromatic alcohol compound is carried out under reaction conditions such that the diaryl ether is formed.

The catalyst is contacted with the aromatic alcohol compound either in the gas phase or in the liquid phase. In addition, the aromatic alcohol may be diluted with a diluent or it may be neat. Suitable diluents include, without limitation, nitrogen, argon, water vapor, water, oxygen or hydrogen. When a diluent is used, the concentration of the aromatic alcohol compound may be, for instance, 1 volume percent or greater and less than 100 volume percent.

In a preferred embodiment, the aromatic alcohol is contacted with the catalyst in the gas phase. Typically, the aromatic alcohol is introduced into a reactor containing the catalyst at elevated temperature, for instance, between 200 and 800° C., alternatively between 250 and 600° C., or alternatively between 400 and 600° C. The reaction may be conducted at atmospheric pressure, under reduced pressure, or at elevated pressure such as up to 5000 psi. In some embodiments, atmospheric pressure or slightly above (e.g., up to about 50 psi) is preferred. In some embodiments, the gas flow rate of the aromatic alcohol over the catalyst (weighted hourly space velocity or WHSV) is from 0.01 to 100 grams per hour per gram (g/g·h). In some embodiments, WHSV is from 0.1 to 20 g/g·h, alternatively 0.1 to 5 g/g·h, or alternatively 0.1 to 1 g/g·h.

In some embodiments, it may be useful to subject the reactor to startup conditions which may provide various benefits, such as prolonging catalyst life. Suitable startup condition include, for example, exposing the catalyst to dilute amounts of the aromatic alcohol at lower temperature before changing to full operating conditions as described above and demonstrated by the examples.

Following the reaction, the diaryl ether product is recovered from the catalyst and optionally further purified. Unreacted alcohol and other reaction by-products may be separated using methods known in the art. Such methods include but are not limited to distillation, crystal refining, simulated moving bed technique or a combination thereof.

In some embodiments, the diaryl ether prepared by the process of the invention is diphenyl oxide (DPO). Other diaryl ether compounds that may be prepared by the process of the invention include, without limitation, compounds containing at least one ether functionality whereby two aryl moieties are connected by an oxygen atom (Ar—O—Ar), including polyaryl compounds and compounds prepared from the aromatic alcohols described above. Specific examples include, but are not limited to, phenoxytoluene isomers, including 3-phenoxytoluene, ditolyl ether isomers, polyphenyl ethers (PPEs), biphenylphenyl ether isomers and naphthyl phenyl ethers.

The diaryl ethers prepared by the invention are useful in a variety of applications, including as high temperature solvents, as intermediates in preparing flame retardants and surfactants, and as components in heat transfer fluids. Furthermore, certain diaryl ethers prepared by the invention are useful as high performance lubricants and as intermediates in preparing pyrethroid insecticides.

In some embodiments, a preferred use of the diaryl ether is in high temperature heat transfer fluids. High temperature heat transfer fluids may be prepared by making the diaryl ether according to the process described above and then mixing the diaryl ether with biphenyl. The amounts necessary to provide a suitable fluid can be readily determined by a person with ordinary skill in the art. For diphenyl oxide and biphenyl, the amount of DPO may be, for instance, from 70 to 75 weight percent based on the total weight of the DPO and biphenyl. A preferred amount of DPO is that required to form a eutectic mixture with the biphenyl, which is about 73.5 weight percent based on the total weight of the DPO and biphenyl.

Some embodiments of the invention will now be described in detail in the following Examples.

EXAMPLES

Example 1

Dehydration of Phenol with Yttrium Oxide/Chloride

In this example, neat yttrium oxide containing 2 percent chloride is used for the conversion of phenol to diphenyl oxide (DPO). The oxide is obtained from a commercial vendor. The powder is pressed and sieved to obtain particles that are between 0.60 mm and 0.85 mm in diameter. The particles are loaded into an electrically heated stainless steel reactor tube and heated to the reaction temperature with nitrogen flowing through the tube. After the reaction temperature is reached, vapor-phase phenol is passed through the reactor tube. The conversion of phenol (either neat or diluted with an inert gas) is carried out under varied weighted hourly space velocities (WHSV=gram phenol/gram catalyst·hour) and temperature conditions. Tables 1 and 2 show test conditions and results obtained.

TABLE 1

| Test Conditions | Conversion [mol. %] Phenol Conversion | Selectivity [mol. %] | | | | | |
|---|---|---|---|---|---|---|---|
| | | Diphenyl Oxide | OPP | DBF | O-BIPPE | M-BIPPE | P-BIPPE |
| T = 400° C. Feed: PhOH/N2 = 1/0.2 ToS = 2 hrs WHSV 1 hr$^{-1}$ | 0.06% | 100.00% | 0.00% | 0.00% | 0.00% | 0.00% | 0.00% |
| T = 500° C. Feed: PhOH/N2 = 1/0.2 ToS = 4.5 hrs WHSV 1 hr$^{-1}$ | 6.61% | 96.35% | 0.00% | 3.64% | 0.00% | 0.00% | 0.00% |
| T = 500° C. Feed: PhOH ToS = 4.5 hrs WHSV 0.1 hr$^{-1}$ | 33.3% | 93.0% | 0.00% | 6.9% | 0.02% | 0.03% | 0.11% |
| T = 500° C. Feed: PhOH ToS = 28.5 hrs WHSV 0.1 hr$^{-1}$ | 34.9% | 94.9% | 0.01% | 4.85% | 0.00% | 0.20% | 0.08% |
| T = 500° C. Feed: PhOH ToS = 47.5 hrs WHSV 0.1 hr$^{-1}$ | 32.6% | 94.5% | 0.04% | 5.2% | 0.03% | 0.18% | 0.07% |

Feed: volumetric flow rate;
OPP = orthophenylphenol;
DBF = dibenzofuran;
O-BIPPE = ortho-biphenylphenyl ether;
M-BIPPE = meta-biphenylphenyl ether;
P-BIPPE = para-biphenylphenyl ether;
PhOH = phenol;
N2 = nitrogen;
ToS = time on stream (ToS = 0 hours defined at start of phenol flow)

TABLE 2

Dilute phenol feed at a range of temperatures.

| WHSV (wt PhOH/ wt cat · hr) | Feed Composition (vol. %) | Temperature (° C.) | Phenol Conversion | DPO Selectivity (%) | DBF Selectivity (%) |
|---|---|---|---|---|---|
| 0.1 | 33% PhOH 67% N2 | 400 | 1.78 | 96.95 | 3.03 |
| 0.1 | 33% PhOH 67% N2 | 450 | 5.89 | 96.64 | 3.35 |
| 0.1 | 33% PhOH 67% N2 | 500 | 17.17 | 94.92 | 4.97 |

TABLE 3

Neat phenol feed at a range of temperatures.

| WHSV (wt PhOH/ wt cat · hr) | Feed Composition (vol. %) | Temperature (° C.) | Phenol Conversion | DPO Selectivity (%) | DBF Selectivity (%) |
|---|---|---|---|---|---|
| 0.1 | 100% PhOH | 400 | 2.85 | 92.57 | 7.24 |
| 0.1 | 100% PhOH | 450 | 10.73 | 91.56 | 8.24 |
| 0.1 | 100% PhOH | 500 | 28.47 | 91.1 | 8.73 |
| 0.6 | 100% PhOH | 550 | 35.92 | 85.16 | 14.41 |

TABLE 4

Neat phenol feed at a range of space velocities.

| WHSV (wt PhOH/ wt cat · hr) | Feed Composition (vol. %) | Temperature (° C.) | Phenol Conversion | DPO Selectivity (%) | DBF Selectivity (%) |
|---|---|---|---|---|---|
| 0.1 | 100% PhOH | 500 | 28.47 | 91.1 | 8.73 |
| 0.3 | 100% PhOH | 500 | 18.1 | 89.1 | 10.36 |
| 0.6 | 100% PhOH | 500 | 10.48 | 93.04 | 6.8 |
| 1.0 | 100% PhOH | 500 | 6.61 | 97.35 | 3.64 |

TABLE 5

Gentle startup: 400° C. for 5 hours then 450° C. for 5 more hours in dilute phenol feed. Change to neat phenol and increase temperature to 500° C.

| WHSV (wt PhOH/ wt cat · hr) | Feed Composition (vol. %) | Temperature (° C.) | Phenol Conversion | DPO Selectivity (%) | DBF Selectivity (%) |
|---|---|---|---|---|---|
| 0.1 | 100% PhOH | 500 | 32.47 | 92.94 | 6.82 |

Example 2

Dehydration of Phenol with Yttrium Oxide (no Chloride)

A solution of yttrium nitrate is made by dissolving 86.7 g Y(NO$_3$)$_3$·4H$_2$O in 1000 mL deionized H$_2$O. This solution is added dropwise over one hour into a four liter beaker with an overhead stirrer running at 375 RPM. While the yttrium solution is added, the pH of the solution is maintained near 9.0 by adding ammonium hydroxide solution with a concentration of 14.6 mol NH$_3$/liter H$_2$O dropwise as needed. After the yttrium solution is added, half of the slurry solution is filtered using vacuum filtration in a Buchner funnel. The solid is dispersed in one liter of H$_2$O, filtered, dispersed in a second liter of H$_2$O, and filtered again. The solid is then dried at 110° C. for four hours, then the temperature is increased to 600° C. at a rate of 5° C./min held for four hours, and allowed to cool to room temperature.

The solid is tested for phenol dehydration following the procedure in Example 1 and the results are reported in Table 6.

Example 3

Dehydration of Phenol with Yttrium Oxychloride

A solution of yttrium trichloride is made by dissolving 50.03 g yttrium trichloride hexahydrate in 165 mL deionized H$_2$O. This solution is added dropwise over one hour into a two liter beaker already containing 400 mL deionized H$_2$O with an overhead stirrer running at 375 RPM. While the yttrium solution is added, the pH of the solution is maintained at a constant 9.0 by adding ammonium hydroxide solution with a concentration of 14.6 mol NH$_3$/liter H$_2$O dropwise as needed. After the yttrium solution is added the solution is aged for an additional one hour with the pH maintained at 9.0 by adding additional ammonium hydroxide solution. The solid precipitate is separated from the solution using vacuum filtration in a Buchner funnel. The solid is dried in an oven for 16 hours at 120° C. Eight grams of the dried sample are then treated in an oven at 120° C. for four hours then the temperature is increased to 500° C. at a rate of 5° C./min, held for four hours, and allowed to cool to room temperature. The resulting sample contains 16.1 wt. % chlorine as measured by neutron activation analysis. The solid is tested for phenol dehydration following the procedure in Example 1 and the results are reported in Table 6.

Example 4

Dehydration of Phenol with Yttrium Oxide with HCl Added

A solution of yttrium nitrate is made by dissolving 80.1 g Y(NO$_3$)$_3$·4H$_2$O in 800 g deionized H$_2$O in a two liter beaker with magnetic stirring at 400 RPM. Ammonium hydroxide solution with a concentration of 14.6 mol NH$_3$/liter H$_2$O is added dropwise until a pH of 9.0 is reached. The slurry solution is put into a one liter polypropylene bottle and heated to 100° C. for 70 hours in an oven. After cooling to room temperature, the solution is filtered, dispersed in 1000 mL of H$_2$O, and filtered again. The solid is then dried at 110° C. for 16 hours, then the temperature is increased to 600° C. at a rate of 5° C./min held for three hours, and allowed to cool to room temperature. 0.4703 g of an HCl solution with a concentration of 12 mols HCl/liter H$_2$O is added to 1.668 mL of deionized H$_2$O and then added with mixing to 2.0 g of the dried solid. The solid is then dried at 120° C. for four hours, the temperature is then increased to 400° C. at a rate of 5° C./min held for four hours and allowed to cool to room temperature. The solid is tested for phenol dehydration following the procedure in Example 1 and the results are reported in Table 6.

Example 5

Dehydration of Phenol with Yttrium Oxide with NH$_4$Cl Added

A solution of yttrium nitrate is made by dissolving 80.1 g Y(NO$_3$)$_3$·4H$_2$O in 800 g deionized H$_2$O in a two liter beaker with magnetic stirring at 400 RPM. Ammonium hydroxide solution with a concentration of 14.6 mol NH$_3$/liter H$_2$O is added dropwise until a pH of 9.0 is reached. The slurry solution is put into a one liter polypropylene bottle and heated to 100° C. for 70 hours in an oven. After cooling to room temperature, the solution is filtered, dispersed in 1000 mL of H$_2$O, and filtered again. The solid is then dried at 110° C. for 16 hours, then the temperature is increased to 600° C. at a rate of 5° C./min held for three hours, and allowed to cool to room temperature. 0.063 g of NH$_4$Cl is dissolved in 2.0 mL of deionized H$_2$O and then added with mixing to 2.0 g of the dried solid. The solid is then dried at 120° C. for four hours, the temperature is then increased to 400° C. at a rate of 5° C./min held for four hours and allowed to cool to room temperature. The solid is tested for phenol dehydration following the procedure in Example 1 and the results are reported in Table 6.

TABLE 6

Phenol dehydration on yttrium containing samples.

| Sample | WHSV (wt PhOH/ wt cat · hr) | Feed Composition (vol. %) | Temperature (° C.) | Phenol Conversion | DPO Selectivity (%) | DBF Selectivity (%) |
|---|---|---|---|---|---|---|
| Ex. 2 | 1.0 | 100% PhOH | 500 | 0.28 | 51.0 | 46.4 |
| Ex. 3 | 1.0 | 100% PhOH | 500 | 8.2 | 99.2 | 0.8 |
| Ex. 4 | 1.0 | 100% PhOH | 500 | 8.9 | 97.2 | 2.7 |
| Ex. 5 | 1.0 | 100% PhOH | 500 | 6.5 | 96.9 | 3.1 |

Example 6

Dehydration of Phenol with Yttrium Oxychloride

A solution of yttrium trichloride is made by dissolving 50.0 g yttrium trichloride hexahydrate in 165 mL deionized $H_2O$. This solution is added dropwise over 15 minutes into a two-liter beaker already containing 400 mL deionized $H_2O$ with an overhead stirrer running at 375 RPM. While the yttrium solution is added, the pH of the solution is maintained at a constant 9.0 by adding a tetrapropylammonium hydroxide solution with a concentration of 40 wt. % tetrapropylammonium hydroxide in water as needed. After the yttrium solution is added, the solution is aged for an additional one hour with the pH maintained at 9.0 by adding additional tetrapropylammonium hydroxide solution. The solid precipitate is separated from the solution by centrifugation at 7000 RPM for five minutes and decanting off the liquid. The solid is dried in a loosely covered container in an oven for four hours at 120° C. then the temperature is increased to 500° C. at a rate of 5° C./min, held for four hours, and allowed to cool to room temperature. The resulting sample contains 11.5 wt. % chlorine as measured by neutron activation analysis.

The solid is tested for phenol dehydration by loading a portion into an electrically heated stainless steel reactor tube and heated to the reaction temperature with nitrogen flowing through the tube. After the reaction temperature is reached, vapor-phase phenol is passed through the reactor tube. The conversion of phenol (either neat or diluted with an inert gas) is carried out under varied weighted hourly space velocities (WHSV=gram phenol/gram catalyst·hour) and temperature conditions. Table 7 shows test conditions and results obtained.

TABLE 7

| WHSV (wt PhOH/ wt cat · hr) | Feed Composition (vol. %) | Temperature (° C.) | Phenol Conversion | DPO Selectivity (%) | DBF Selectivity (%) |
|---|---|---|---|---|---|
| 1 | 100% PhOH | 500 | 28.51 | 98.65 | 1.21 |
| 0.5 | 100% PhOH | 400 | 1.11 | 98.68 | 1.32 |
| 0.5 | 100% PhOH | 450 | 8.54 | 98.99 | 0.86 |

Example 7

Dehydration of Phenol with Yttrium Oxychloride

A solution of yttrium trichloride is made by dissolving 50.0 g yttrium trichloride hexahydrate in 165 mL deionized $H_2O$. This solution is added dropwise over 15 minutes into a two-liter beaker already containing 400 mL deionized $H_2O$ with an overhead stirrer running at 375 RPM. While the yttrium solution is added, the pH of the solution is maintained at a constant 9.0 by adding a tetraethylammonium hydroxide solution with a concentration of 35 wt. % tetraethylammonium hydroxide in water as needed. After the yttrium solution is added, the solution is aged for an additional one hour with the pH maintained at 9.0 by adding additional tetraethylammonium hydroxide solution. The solid precipitate is separated from the solution by centrifugation at 7000 RPM for five minutes and decanting off the liquid. The solid is dried in a loosely covered container in an oven for four hours at 120° C. then the temperature is increased to 500° C. at a rate of 5° C./min, held for four hours, and allowed to cool to room temperature. The resulting sample contains 13.3 wt. % chlorine as measured by neutron activation analysis.

The solid is tested for phenol dehydration by loading a portion into an electrically heated stainless steel reactor tube and heated to the reaction temperature with nitrogen flowing through the tube. After the reaction temperature is reached, vapor-phase phenol is passed through the reactor tube. The conversion of phenol (either neat or diluted with an inert gas) is carried out under varied weighted hourly space velocities (WHSV=gram phenol/gram catalyst·hour) and temperature conditions. Table 8 shows test conditions and results obtained.

TABLE 8

| WHSV (wt PhOH/ wt cat · hr) | Feed Composition (vol. %) | Temperature (° C.) | Phenol Conversion | DPO Selectivity (%) | DBF Selectivity (%) |
|---|---|---|---|---|---|
| 1 | 100% PhOH | 500 | 12.83 | 99.48 | 0.44 |

Example 8

Dehydration of Phenol with Yttrium Oxyfluoride

Preparation of the bulk yttrium oxide catalyst precursor, $Y_2O_3$. A solution of yttrium nitrate is made by dissolving 80.1 g $Y(NO_3)_3 \cdot 4H_2O$ in 800 mL deionized $H_2O$ into a four-liter beaker with an overhead stirrer running at 400 RPM. A white precipitate forms as the pH of the solution is adjusted to 9.0 by adding ammonium hydroxide solution with a concentration of 14.6 mol $NH_3$/liter. The slurry is transferred to a one-liter sealed container and heated at 100° C. for 70 hours. The slurry solution is cooled to room temperature and filtered using vacuum filtration in a Buchner funnel. The solid is dispersed in one liter of $H_2O$, filtered, dispersed in a second liter of $H_2O$, and filtered again. The solid is then dried at 110° C. for 18 hours, then the temperature is increased to 600° C. at a rate of 5° C./min held for four hours, and allowed to cool to room temperature.

Preparation of fluoride-activated yttrium oxide using ammonium fluoride. A solution of ammonium fluoride is made by dissolving 0.234 g NH₄F in 2.859 mL deionized H₂O. The ammonium fluoride solution is then added to 3.0 g of bulk yttrium oxide precursor dropwise with constant stirring using a spatula. The sample is then dried in air at 120° C. for four hours and then temperature is increased to 400° C. with a ramp rate of 5° C./min and held for four hours.

The particles are loaded into an electrically heated stainless steel reactor tube and heated to the reaction temperature with nitrogen flowing through the tube. After the reaction temperature is reached, vapor-phase phenol is passed through the reactor tube. The conversion of phenol (either neat or diluted with an inert gas) is carried out under varied weighted hourly space velocities (WHSV=gram phenol/gram catalyst·hour) and temperature conditions. Table 9 shows test conditions and results obtained.

TABLE 9

| WHSV (wt PhOH/ wt cat · hr) | Feed Composition (vol. %) | Temperature (° C.) | Phenol Conversion | DPO Selectivity (%) | DBF Selectivity (%) |
|---|---|---|---|---|---|
| 1 | 100% PhOH | 500 | 0.37 | 91.55 | 8.44 |

Example 9

Dehydration of Phenol with Supported Yttrium Oxide Doped with Fluorine

The synthesis of supported yttrium oxide doped with fluorine is carried out via an incipient wetness impregnation of amorphous silica loaded with magnesia.

Precursors:

Support: amorphous silica Davison 57, 30-60 mesh size, that has been loaded with magnesia (6.4 wt. % Mg) characterized to BET=212.14 m²/g that exhibits an incipient wetness condition of approximately 0.90 mL per 1 g.

Solution: Yttrium(III) nitrate hexahydrate (Y(NO₃)₃.6H₂O) and deionized water (DI water), prepared to c=1.25 mol/L.

Ammonium fluoride (NH₄F) and deionized water (DI water), prepared to c=1.25 mol/L.

Synthesis:

4.5 mL of the yttrium nitrate solution is added dropwise to 5 g of support at ambient conditions under vigorous shaking using a shaker plate. The impregnated material is then dried at 150° C. for one hour, and the impregnation procedure is repeated using the solution of ammonium fluoride (4.5 mL). The preparation is finished off by calcining the impregnated material in a static air calcination oven using the following protocol: ramp 1.66° C./min; dwell at T=550° C. for 3 hours, cool down to room temperature.

Catalytic Test:

The particles are loaded into an electrically heated stainless steel reactor tube and heated to the reaction temperature with nitrogen flowing through the tube. After the reaction temperature is reached, vapor-phase phenol is passed through the reactor tube. The conversion of phenol (either neat or diluted with an inert gas) is carried out under varied weighted hourly space velocities (WHSV=gram phenol/gram catalyst·hour) and temperature conditions. Table 10 shows test conditions and results obtained.

TABLE 10

| WHSV (wt PhOH/ wt cat · hr) | Feed Composition (vol. %) | Temperature (° C.) | Phenol Conversion | DPO Selectivity (%) | DBF Selectivity (%) |
|---|---|---|---|---|---|
| 1 | 100% PhOH | 500 | 1.15 | 82.7 | 15.3 |

Example 10

Dehydration of Phenol with Y2(HPO4)3

A solution of yttrium nitrate is made by dissolving 38.3 g yttrium nitrate hexahydrate in 500 mL deionized H₂O. A separate solution of ammonium phosphate dibasic is made by dissolving 19.81 g (NH₄)₂HPO₄ in 500 mL deionized water. The solutions are combined and a precipitate forms. The solid precipitate is separated from the solution by vacuum filtration, redispersed in 1 liter of deionized water and vacuum filtered again. The solid is dried in an oven for 16 hours at 120° C. then the temperature is increased to 400° C. at a rate of 5° C./min, held for four hours, and allowed to cool to room temperature.

The particles are loaded into an electrically heated stainless steel reactor tube and heated to the reaction temperature with nitrogen flowing through the tube. After the reaction temperature is reached, vapor-phase phenol is passed through the reactor tube. The conversion of phenol (either neat or diluted with an inert gas) is carried out under varied weighted hourly space velocities (WHSV=gram phenol/gram catalyst·hour) and temperature conditions. Table 11 shows test conditions and results obtained.

TABLE 11

| WHSV (wt PhOH/ wt cat · hr) | Feed Composition (vol. %) | Temperature (° C.) | Phenol Conversion | DPO Selectivity (%) | DBF Selectivity (%) |
|---|---|---|---|---|---|
| 1 | 100% PhOH | 500 | 0.25 | 83.78 | 16.13 |

Example 11

Dehydration of Phenol with Yttria on Zirconia

Preparation of zirconia-supported yttrium oxide precursor. A solution of zirconyl chloride is made by dissolving 161.05 g ZrOCl₂ in 2 L deionized H₂O. Solution is added over 1 hour into a 4-L beaker with an overhead stirrer running at 400 RPM starting with 500 mL deionized H₂O. Ammonium hydroxide solution with a concentration of 14.6 mol NH₃/liter is added as needed to maintain a pH of 10.0 in the solution. A white precipitate is formed and is separated from the liquid by centrifugation for 45 minutes at 3000 rpm and decanting the liquid. The solids are then redispersed in one liter of 60° C. deionized H₂O and the pH is adjusted to 10.0 using ammonium hydroxide. The solids are then separated again by centrifugation and the washing process is repeated four times. The zirconium oxyhydroxide solids are then dried at 120° C. for eighteen hours. A solution of yttrium nitrate is made by adding 0.244 mL deionized water to 1.106 mL of a 0.5 mol/liter aqueous yttrium nitrate solution. The yttrium nitrate solution is then added dropwise with constant stirring using a spatula to 5.0 g of zirconium oxyhydroxide produced in the previous step. The sample is then dried in air at 110° C. for four hours and then the temperature is increased to 600° C. with a ramp rate of 5° C./min, held for four hours, and cooled to room temperature.

Preparation of chloride-activated yttrium oxide using aqueous hydrogen chloride. A solution of hydrogen chloride is made by mixing 0.294 mL HCl (10 mol/L) with 0.144 mL deionized $H_2O$. The hydrogen chloride solution is then added dropwise with constant stirring using a spatula to 3.0 g of zirconia supported yttrium oxide precursor prepared using the method above. The sample is then dried in air at 120° C. for four hours and then temperature is increased to 400° C. with a ramp rate of 5° C./min, held for four hours, and cooled to room temperature.

The particles are loaded into an electrically heated stainless steel reactor tube and heated to the reaction temperature with nitrogen flowing through the tube. After the reaction temperature is reached, vapor-phase phenol is passed through the reactor tube. The conversion of phenol (either neat or diluted with an inert gas) is carried out under varied weighted hourly space velocities (WHSV=gram phenol/gram catalyst·hour) and temperature conditions. Table 12 shows test conditions and results obtained.

TABLE 12

| WHSV (wt PhOH/ wt cat · hr) | Feed Composition (vol. %) | Temperature (° C.) | Phenol Conversion | DPO Selectivity (%) | DBF Selectivity (%) |
|---|---|---|---|---|---|
| 1 | 100% PhOH | 500 | 4.28 | 88.76 | 10.22 |

Example 12

Dehydration of Phenol with KCl-doped Yttria

The synthesis of bulk yttrium oxide surface-doped with potassium chloride is carried out via an incipient wetness impregnation of yttrium oxide.
Precursors:
Bulk yttrium oxide is prepared via thermal decomposition of yttrium carbonate (temperature ramp 1.41° C./min; T=550° C.; dwell time 3 hours) and exhibits an incipient wetness condition of approximately 1.2 mL per 1 g characterized to BET surface area of 53.4 $m^2/g$.
Solution: Potassium chloride (KCl) and deionized water (DI water), prepared to c=0.4702 mol/L.
Synthesis:
1.2 mL of the solution is added dropwise to 1 g of support at ambient conditions under vigorous shaking using a shaker plate. The impregnated material is then dried at 150° C. for one hour. The preparation is finished off by calcining the impregnated material in a static air calcination oven using the following protocol: ramp 1° C./min; dwell at T=550° C. for 3 hours, cool down to room temperature. The chlorine content of the catalyst is assayed by XRF to 3.83 wt. % chlorine.
The particles are loaded into an electrically heated stainless steel reactor tube and heated to the reaction temperature with nitrogen flowing through the tube. After the reaction temperature is reached, vapor-phase phenol is passed through the reactor tube. The conversion of phenol (either neat or diluted with an inert gas) is carried out under varied weighted hourly space velocities (WHSV=gram phenol/gram catalyst·hour) and temperature conditions. Table 13 shows test conditions and results obtained.

TABLE 13

| WHSV (wt PhOH/ wt cat · hr) | Feed Composition (vol. %) | Temperature (° C.) | Phenol Conversion | DPO Selectivity (%) | DBF Selectivity (%) |
|---|---|---|---|---|---|
| 1 | 100% PhOH | 500 | 4.26 | 98.09 | 1.82 |

Example 13

Dehydration of Phenol with supported Yttrium Oxychloride

The synthesis of supported yttrium oxychloride is carried out via an incipient wetness impregnation of gamma alumina.
Precursors:
Support: gamma alumina (available from Saint-Gobain NorPro) 30-60 mesh size, BET=178.9 $m^2/g$) that exhibits an incipient wetness condition of approximately 0.75 mL per 1 g.
Solution: Yttrium(III) chloride hexahydrate ($YCl_3·6H_2O$) and deionized water (DI water), prepared to c=0.75 mol/L.
Synthesis:
3.75 mL of the solution is added dropwise to 5 g of support at ambient conditions under vigorous shaking using a shaker plate. The impregnated material is then dried at 150° C. for one hour, and the impregnation procedure is repeated three more times (total of 4×3.75 mL used for 5 g of carrier) to achieve a high loading of yttrium inside the pores of the carrier. The preparation is finished off by calcining the impregnated material in a static air calcination oven using the following protocol: ramp 1° C./min; dwell at T=550° C. for 3 hours, cool down to room temperature. The chlorine content of the catalyst is assayed by XRF to 4.9 wt. % chlorine.
Catalytic Test:
The particles are loaded into an electrically heated stainless steel reactor tube and heated to the reaction temperature with nitrogen flowing through the tube. After the reaction temperature is reached, vapor-phase phenol is passed through the reactor tube. The conversion of phenol (either neat or diluted with an inert gas) is carried out under varied weighted hourly space velocities (WHSV=gram phenol/gram catalyst·hour) and temperature conditions. Table 14 shows test conditions and results obtained.

TABLE 14

| WHSV (wt PhOH/ wt cat · hr) | Feed Composition (vol. %) | Temperature (° C.) | Phenol Conversion | DPO Selectivity (%) | DBF Selectivity (%) |
|---|---|---|---|---|---|
| 1 | 100% PhOH | 500 | 2.96 | 82.17 | 16.09 |

Example 14

Dehydration of Phenol with Supported Yttrium Oxychloride

The synthesis of supported yttrium oxychloride is carried out via an incipient wetness impregnation of amorphous silica.
Precursors:
Support: amorphous silica Davison 57, 30-60 mesh size, BET=275.35 $m^2/g$ that exhibits an incipient wetness condition of approximately 0.90 mL per 1 g.

Solution: Yttrium(III) chloride hexahydrate ($YCl_3 \cdot 6H_2O$) and deionized water (DI water), prepared to c=1.25 mol/L.
Synthesis:
4.5 mL of the solution is added dropwise to 5 g of support at ambient conditions under vigorous shaking using a shaker plate. The impregnated material is then dried at 150° C. for one hour, and the impregnation procedure is repeated one more time (total of 2×4.50 mL used for 5 g of carrier) to achieve a high loading of yttrium inside the pores of the carrier. The preparation is finished off by calcining the impregnated material in a static air calcination oven using the following protocol: ramp 1° C./min; dwell at T=550° C. for 3 hours, cool down to room temperature. The chlorine content of the catalyst is assayed by XRF to 1.55 wt. % chlorine.
Catalytic Test:
The particles are loaded into an electrically heated stainless steel reactor tube and heated to the reaction temperature with nitrogen flowing through the tube. After the reaction temperature is reached, vapor-phase phenol is passed through the reactor tube. The conversion of phenol (either neat or diluted with an inert gas) is carried out under varied weighted hourly space velocities (WHSV=gram phenol/gram catalyst·hour) and temperature conditions. Table 15 shows test conditions and results obtained.

TABLE 15

| WHSV (wt PhOH/ wt cat · hr) | Feed Composition (vol. %) | Temperature (° C.) | Phenol Conversion | DPO Selectivity (%) | DBF Selectivity (%) |
|---|---|---|---|---|---|
| 1 | 100% PhOH | 500 | 2.42 | 87.8 | 11.5 |

What is claimed is:

1. A method for preparing a diaryl ether, the method comprising dehydrating an aromatic alcohol compound over a dehydration catalyst, wherein the dehydration catalyst comprises an oxide of yttrium and further comprises halide ion.

2. The method of claim 1 wherein the halide ion is chloride or fluoride.

3. The method of claim 1 wherein the dehydration catalyst further comprises a binder.

4. The method of claim 1 wherein the dehydration catalyst is supported.

5. The method of claim 1 wherein the dehydration catalyst is unsupported.

6. The method of claim 1 wherein the dehydration of the alcohol is conducted at a temperature from 250 to 600° C.

7. The method of claim 1 wherein the alcohol feed is diluted with a diluent.

8. The method of claim 1 wherein the aromatic alcohol compound is phenol and the diaryl ether produced is diphenyl oxide.

9. A method for producing a heat transfer fluid, the method comprising:
preparing a diaryl ether by contacting an aromatic alcohol compound with a dehydration catalyst, wherein the dehydration catalyst comprises an oxide of yttrium and further comprises halide ion;
isolating the diaryl ether from the dehydration catalyst; and
mixing the isolated diaryl ether with biphenyl, wherein the mixture forms a eutectic mixture.

* * * * *